(12) United States Patent
Larsen

(10) Patent No.: US 7,928,718 B2
(45) Date of Patent: Apr. 19, 2011

(54) METHOD FOR CALIBRATING A PARTICLE COUNTING APPARATUS

(75) Inventor: Ulrik Darling Larsen, Lyngby (DK)

(73) Assignee: Chempaq A/S, Farum (DK)

(*) Notice: Subject to any disclaimer, the term of this patent is extended or adjusted under 35 U.S.C. 154(b) by 514 days.

(21) Appl. No.: 11/664,170

(22) PCT Filed: Sep. 30, 2005

(86) PCT No.: PCT/DK2005/000622
§ 371 (c)(1),
(2), (4) Date: Jun. 4, 2007

(87) PCT Pub. No.: WO2006/037325
PCT Pub. Date: Apr. 13, 2006

(65) Prior Publication Data
US 2008/0031780 A1 Feb. 7, 2008

(30) Foreign Application Priority Data
Oct. 1, 2004 (DK) .................................. 2004 01500

(51) Int. Cl.
*G01N 27/00* (2006.01)
*G06M 11/02* (2006.01)
(52) U.S. Cl. .................. 324/71.4; 324/71.1; 377/12
(58) Field of Classification Search ............. 324/71.1, 324/71.4; 377/12
See application file for complete search history.

(56) References Cited

U.S. PATENT DOCUMENTS

| | | | |
|---|---|---|---|
| 3,259,842 A | | 7/1966 | Coulter et al. |
| 3,345,502 A | * | 10/1967 | Berg et al. .................. 377/11 |
| 3,530,381 A | * | 9/1970 | Klein et al. ................ 324/71.1 |
| 3,638,227 A | | 1/1972 | Angel |
| 3,757,213 A | * | 9/1973 | Coulter et al. ............. 324/71.1 |
| 3,810,011 A | * | 5/1974 | Coulter et al. ............. 324/71.1 |
| 4,338,564 A | | 7/1982 | Mundschenk et al. |
| 6,959,618 B1 | | 11/2005 | Larsen |
| 2003/0020447 A1 | * | 1/2003 | Taylor et al. ............... 324/71.4 |

FOREIGN PATENT DOCUMENTS

| | | | |
|---|---|---|---|
| GB | 1254891 A | | 11/1971 |
| GB | 1254891 A | * | 11/1971 |
| GB | 1371432 A | | 10/1974 |
| WO | WO 0111338 | | 2/2001 |
| WO | WO 2005/022126 A | | 3/2005 |

* cited by examiner

*Primary Examiner* — Timothy J Dole
*Assistant Examiner* — Farhana Hoque
(74) *Attorney, Agent, or Firm* — Volentine & Whitt P.L.L.C.

(57) ABSTRACT

A method of calibration of a particle characterization apparatus, and a particle characterization apparatus, in which particles suspended in a liquid are passed through an orifice one by one for characterization of the particles, for instance by Coulter counting. The calibration does not require utilization of special calibration particles or liquids. A priori knowledge of the shape of a typical size distribution of a blood sample is utilized to adjust the apparatus based on an initial relatively short counting period of the sample in question. The initially determined size distribution is compared to the corresponding known typical size distribution and the apparatus is subsequently adjusted to counteract possible differences. Upon adjustment of the apparatus, the remaining part of the sample is passed through the orifice for determination of the actual particle size distribution of the remaining sample.

2 Claims, 6 Drawing Sheets

| COUNTER | LOWER THRESHOLD (mV) | UPPER THRESHOLD (mV) | CELL IDENTIFICATION |
|---|---|---|---|
| W0 | 200 | 330 | No Cells |
| W1 | 330 | 660 | Lymphocytes |
| W2 | 660 | 743 | Monocytes |
| W3 | 743 | 1210 | Granulocytes |
| W4 | 1210 | 1540 | Granulocytes |
| W5 | 1540 | 1650 | Granulocytes |
| W6 | 1650 | 1900 | No Cells |
| W7 | 1900 | over | No Cells |

$$\Delta GAIN = C_1 \cdot \frac{W_4}{W_3 + W_4 + W_5 + W_6} + C_2$$

METHOD FOR CALIBRATING A PARTICLE COUNTING APPARATUS

CROSS REFERENCE TO RELATED APPLICATIONS

This application is the national phase under 35 U.S.C. 371 of PCT International Application No. PCT/DK2005/000622 which has an international filing date of Sep. 30, 2005, and also claims priority under 35 U.S.C. 119 to Danish application PA2004 01500 filed on Oct. 1, 2004, both of which applications are hereby incorporated by reference in their entirety for all purposes as if fully set forth herein.

FIELD OF THE INVENTION

The present invention relates to a particle characterisation apparatus in which particles suspended in a liquid are passed through an orifice, in principle one by one, to enable the characterisation of the particles, for instance by Coulter counting.

BACKGROUND OF THE INVENTION

It is well-known that particles travelling through a small orifice can be characterised with respect to size, concentration and conductivity by the use of an electrical impedance technique, widely known as the Coulter sizing (see V. Kachel, "Electrical Resistance Pulse Sizing Coulter Sizing", Flow Cytometry and Sorting, Second Edition, pp. 45-80, 1990 Wiley-Liss).

Counting and sizing of particles by the impedance principle is an internationally approved method that is being used in most haematology-analysers and particle counting equipment. The method is based on measurable changes in the electrical impedance produced by non-conductive particles in an electrolyte. A small opening, called the "aperture" or "orifice", connects two electrically isolated chambers, where electrodes have been provided to contact the electrolyte. The orifice applies a restriction to the electrical path, whereby a sensing zone is established through which the particles are aspirated. In the sensing zone each particle will give rise to a displacement of the surrounding electrolyte, thus blocking part of the current-path and giving rise to a voltage pulse. By this method several thousand particles per second can be characterised with high precision.

It is also well-known that the peak amplitude of the voltage pulses generated by the particles are closely correlated to the size of the particles, and therefore it is desirable to be able to determine the peak amplitude of voltage pulses in a simple and reliable way and at a low cost.

The haematology analysers are used for counting and differentiating blood cells such as thrombocytes (blood platelets), leucocytes (white blood cells) and Erythrocytes (Red blood cells). The white blood cells can be further characterised by size into the three sub-populations lymphocytes, monocytes and granulocytes.

Typically, known haematology analysers constitute a complete and self-contained apparatus for sequential testing of a large number of blood samples. Such analysers have a relatively complicated flow system with containers for chemicals and rinsing liquids. The flow system is automatically subjected to a rinsing cycle between sample measurements. A calibration sample, e.g. containing polystyrene particles with known diameters may be aspirated into the flow system at regular intervals for calibration of the analyser.

In WO 01/11338, an alternative haematology analyser is disclosed comprising a disposable cartridge and a docking station. The cartridge contains the flow system including the orifice and electrodes for Coulter counting. The docking station interfaces to the flow system and the electrodes and controls the measurement cycle. Blood is sampled by the cartridge, which is then inserted into the docking station for determination of the number of blood cells in the blood sample. Since the cartridge is removed and discarded after testing, the docking station does not need a rinsing system for rinsing of the station between testing of different blood samples whereby a simple and easy to use haematology analyser is provided. This makes it possible to perform measurements near the patient without participation of specialized personnel allowing convenient, accurate monitoring of the state of the patient with a very small delay between sample taking and measurement result.

SUMMARY OF THE INVENTION

It is an object of the present invention to provide a method and a system for calibrating a particle counting apparatus based on the Coulter counting principle that is suitable for use in an apparatus of the type disclosed in WO 01/11338.

It is a further object of the present invention to provide calibration without utilisation of specific calibration particles or liquids.

The pulse height generated by a blood cell in the aperture mainly depends on the size of the particle in relation to the diameter of the aperture or orifice. Thus, in an analyser of the above-mentioned type comprising a cartridge and a docking station, variations in aperture diameters from one cartridge to another create significant pulse height variations for particles of the same size.

In a preferred embodiment of the present invention, the aperture resides in a polymer membrane and is precision machined. Preferably, the aperture is machined with a UV-laser to provide an aperture diameter of 36 μm with a tolerance of ±2%. The aperture to aperture diameter variation (±2%) generates a pulse height variation of the electronic pulses of ±4%, since the pulse height is inversely proportional to the cross sectional area of the aperture, and therefore, it is preferred to calibrate the apparatus before particle size determination.

According to the present invention, it has surprisingly been proven to be possible to calibrate a Coulter counting apparatus based on a priori knowledge of the typical size distribution of a healthy blood sample. Knowledge of the shape of the typical size distribution of, e.g., a human blood sample is utilised to adjust the apparatus based on an initial relatively short counting period of the sample in question. The initially determined size distribution is compared to the corresponding known typical size distribution and the apparatus is subsequently adjusted to counteract possible differences and thereby providing a better fit between the initially determined size distribution and the predetermined typical size distribution. Upon adjustment of the apparatus, the remaining part of the sample is passed through the orifice, such as aspirated through the orifice by applying a low pressure down-stream the orifice, or pumped through the orifice by applying a high pressure up-stream the orifice, for determination of the actual particle size distribution of the remaining sample.

The shape of the size distribution may e.g. be characterized by the position of certain maxima and/or minima of the distribution, or the number of particles within certain ranges of the distribution, etc.

Thus, according to the present invention counting white blood cells and the three sub-populations: Lymphocytes, monocytes and granulocytes, may be performed utilizing pattern recognition without actually determining the exact size of the counted cells. According to the invention, biological and technical variations substantially do not influence the size distribution determination since the cell size distribution is initially determined as a function of an arbitrary, i.e. uncalibrated, size, which is adjusted by identification of certain characteristics of the shape of the distribution.

The size distribution is determined by dividing the relevant size range into an appropriate number of consecutive sub-ranges also denoted bins, and counting the number of particles within each bin.

In a preferred embodiment of the present invention, the bins are not of the same width. Instead, the width of each bin is designed to suit a particle distribution of, e.g., a human blood sample so that the particle distribution, and especially the number of lymphocytes, monocytes and granulocytes, may be determined with a minimum number of bins. A low number of bins also leads to a low resolution of the shape of the determined size distribution, which may be expected to lead to poor calibration. Surprisingly, successful calibration has been proven possible with the method and system according to the present invention with a low number of bins, such as less than 15 bins, preferably less than 12 bins and even more preferred less than 10 bins, such as 8 bins, etc.

An apparatus according to the present invention comprises a pulse height analyser for determination of the pulse height distribution of the electronic pulses generated from Coulter counting. The pulse height of each pulse may for example be determined by recording of the passage of a set of voltage thresholds by the positive going edge of the pulse. The maximum threshold exceeded by each pulse characterises the peak amplitude of the pulse. Identification of the maximum exceeded threshold may for example be input to a micro controller that is adapted to count the number of pulses with identical identifications, i.e. within a bin. Threshold voltages define respective bins. As already mentioned, it is not required that the threshold voltages are equidistant, typically, they are not, and preferably a minimum number of threshold voltages are selected for simple determination of the size distribution in question.

In a preferred embodiment of the invention, each cartridge is calibrated using an initial small part of the sample contained in the cartridge. This has proven to be possible based on a priori knowledge of the typical size distribution of, e.g., a healthy human blood sample. Knowing a typical size distribution, the voltage thresholds can be adjusted based on an initial relatively short counting period of the sample in question. The threshold voltages are adjusted in accordance with possible differences between the initially determined size distribution and the predetermined typical size distribution whereby a better fit between the initially determined size distribution and the predetermined typical size distribution is provided. Upon adjustment of the threshold voltages, the remaining part of the sample is passed, such as aspirated, through the orifice for determination of the actual particle size distribution of the sample in question.

In a preferred embodiment of the invention, the shape of the determined size distribution is characterized by the number of cells in a first set of bins divided by the number of cells in a second set of bins. In the following, the count of the i'th bin $B_i$ is denoted $W_i$ and increasing values of bin number i relate to increasing particle size values. Thus, the shape of the size distribution may be characterised by $$\frac{W_i}{W_j}$$

for selected values of i and j, or by $$\frac{W_i}{W_j + W_k}$$

for specific selected values of i, j and k, or a plurality of selected bins may be incorporated in the nominator and/or a plurality of selected bins may be incorporated in the denominator of the ratio, etc.

In a preferred embodiment of the invention, the voltage pulses are subjected to a gain before comparison with the threshold voltages of the bins, and the gain is adjusted based on a function, such as a linear function, of one of the above-mentioned ratios. The function and ratio have been determined empirically. The measurement sequence comprises the steps of:
a) Short counting for calibration,
b) Calculate the gain,
c) Adjust thresholds to new setting, and
d) Make final count and analyse data.
This is further explained below.

BRIEF DESCRIPTION OF THE DRAWINGS

In the following the invention will be further described and illustrated with reference to the accompanying drawings in which.

DETAILED DESCRIPTION OF PREFERRED EMBODIMENTS

Figure 1:
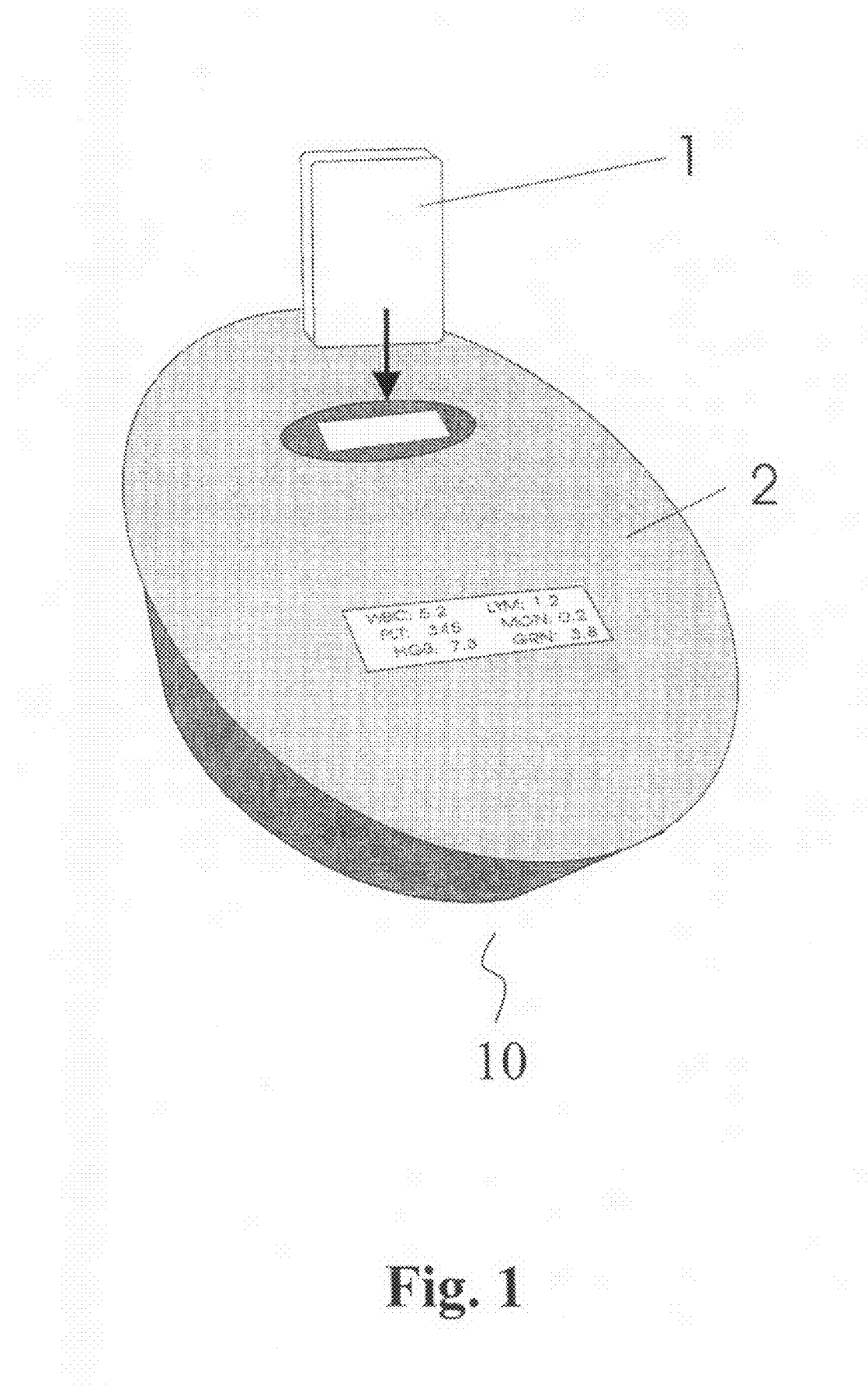
FIG. 1 shows in perspective a haematology analyser according to the present invention

FIG. 1 shows a picture of a Coulter/counting apparatus 10 according to a preferred embodiment of the present invention. The apparatus 10 comprises a disposable cartridge 1 and a docking station 2 for removably receiving the cartridge 1. The cartridge 1 comprises (not shown) a housing with two chambers separated by a wall containing an aperture for the passage of the particles. The cartridge 1 further has an inlet/outlet that interfaces to the docking station 2 for connection to a source of positive or negative gas pressure, and electrodes also interfacing to the docking station 2 for characterizing particles passing through the orifice. Correspondingly, the docking station 2 comprises a port for connection with a source of positive or negative gas pressure and forming a gas connection with the inlet/outlet when the cartridge 1 is received in the docking station 2, and electrical connectors for operative connection with the electrodes when the cartridge 1 is received in the docking station 2. The docking station further comprises a pulse height analyzer for determination of the pulse height distribution of the electronic pulses received from the electrodes in accordance with the Coulter counting principle, and a controller that controls the measurement cycle of the instrument. The controller transmits start and stop signals to the pulse height analyzer. Further, the controller receives the determined size distribution, i.e. the number of particles counted within each bin, from the particle height analyzer. The controller is further adapted to control the calibration cycle as further described below, and to perform the calculations of the adjusted threshold voltages and adjust the voltages accordingly.

Figures 2, 3:
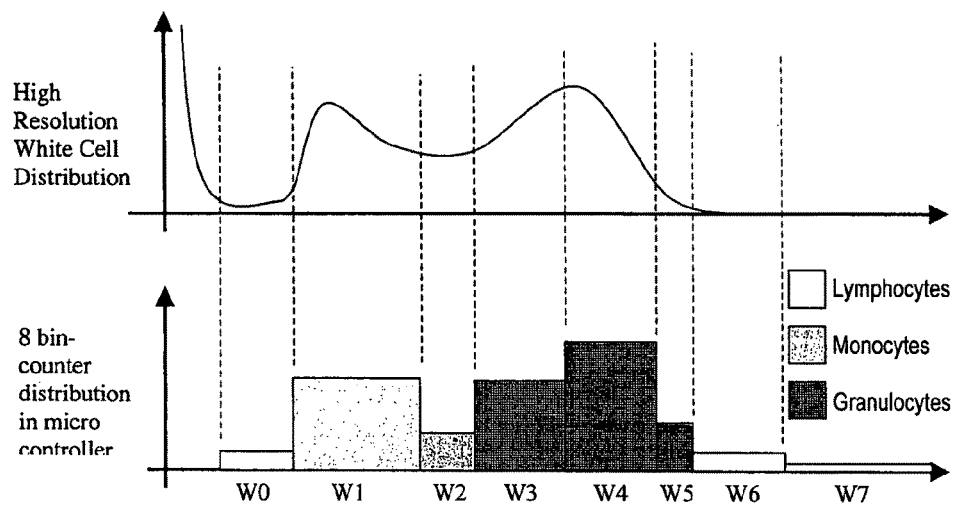
FIG. 2 shows plots of white cell size distributions.
FIG. 3 is a table of selected thresholds for cell bins.

The upper plot of FIG. 2 shows a typical size distribution of white blood cells and the lower part shows the corresponding bins according to a preferred embodiment of the invention. The vertical dashed lines illustrate the bin limits corresponding to the threshold voltages. Bin $B_1$ (particle count $W_1$) contains the lymphocytes, bin $W_2$ (particle count $W_2$) contains the monocytes, and bins $B_3$ (particle count $W_3$), $B_4$ (particle count $W_4$), and $B_5$ (particle count $W_5$) contain the granulocytes. 8 bins are used in this embodiment.

In the present embodiment, the threshold voltages corresponding to the bin limits (the vertical dashed lines) are adjusted relatively with relation to the pulses received from the electrodes in that the pulses are subjected to a gain before comparison with the threshold values. A gain adjustment, ΔGain, corresponds to shifting the bins along the horizontal axis in FIG. 2 by multiplication of bin limits by the reciprocal gain adjustment value $\Delta Gain^{-1}$. As illustrated in FIG. 2, the gain is adjusted to position the upper limit of bin $B_5$ at the upper limit of the nominal size distribution illustrated in the upper plot. The remaining bin limits are then adjusted proportionally to the adjustment of the $B_5$ upper limit.

FIG. 3 is a table of the nominal upper and lower threshold voltages of the eight bins $B_0$ to $B_7$ (particle counts $W_0$ to $W_7$) according to a preferred embodiment of the present invention, i.e. before threshold adjustment.

Figure 4:
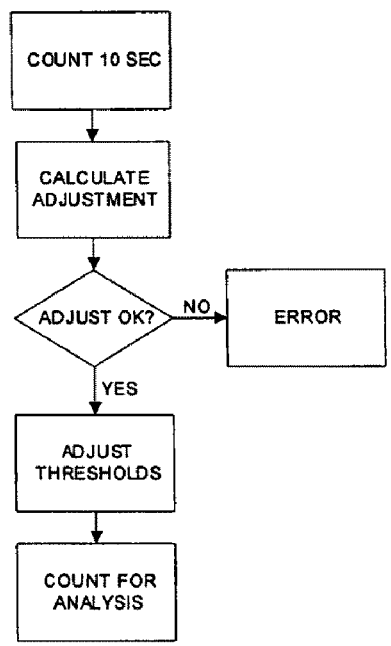
FIG. 4 is a flow chart of a measurement cycle according to the present invention.

A flowchart of a measurement cycle according to a preferred embodiment of the invention is shown in FIG. 4. The controller is adapted for a) controlling the apparatus to count particles contained in a first part of the sample to determine the number of particles in each bin of a predetermined set of bins $W_0$ to $W_7$,
b) adjusting the bin lower and upper limits in accordance with the determined number of particles in each bin and based on a priori knowledge of a typical particle size distribution of the type of sample in question, and
c) counting particles contained in a second part of the sample to determine the number of particles in each adjusted bin.

Figure 5:
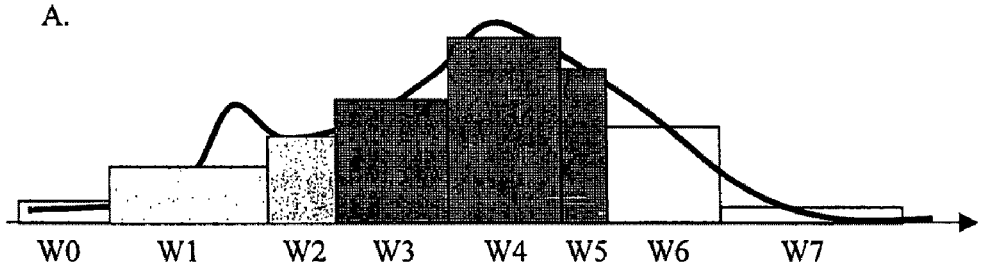
FIG. 5 is a plot of the size distribution before and after thresholds adjustment.
Figure 5:
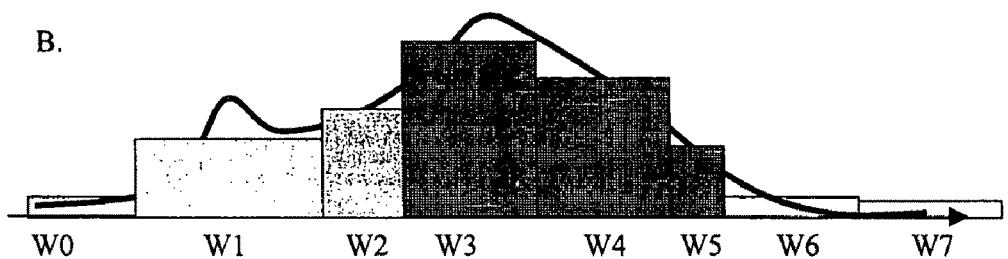

FIG. 5 shows plots of size distributions as determined before (upper plot) and after (lower plot) threshold voltage adjustment. It is seen from the upper plot that the orifice of the cartridge in question has a relatively small diameter so that the pulses received from the electrodes are relatively large stretching the size distribution to the right along the horizontal size axis. Upon calibration, the gain is lowered and the thresholds are placed correctly in relation to the size distribution. The figure illustrates the effect of a varying aperture diameter namely that the size distribution may be stretched or compressed along the horizontal size axis in relation to the bins. This effect is counteracted by the calibration according to the present invention.

Figures 6, 7:
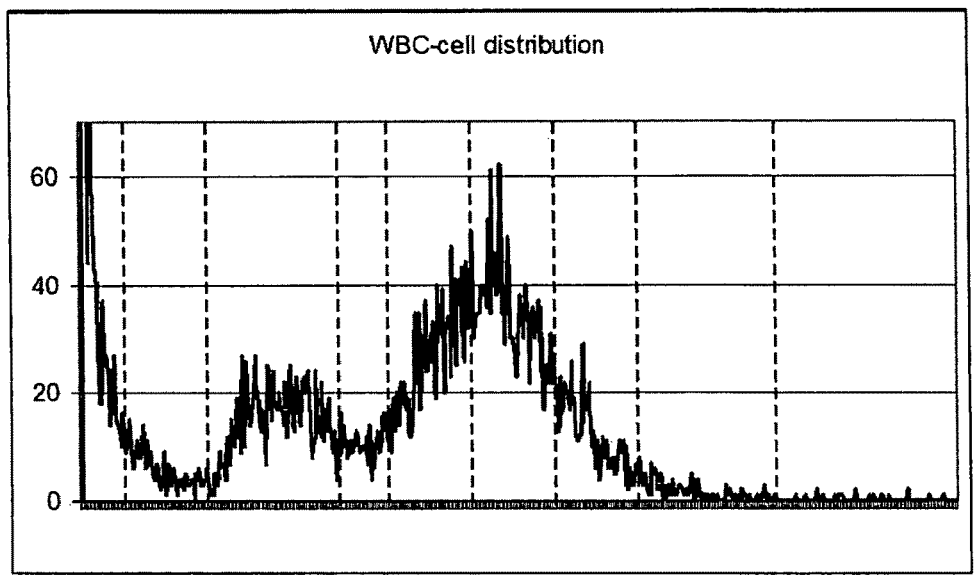
FIG. 6 is a plot of the size distribution with the visual identification of the maximum size of granulocytes indicated.
FIG. 7 is a preferred algorithm according to the present invention.

FIG. 6 shows a plot of a typical size distribution of white blood cells or leucocytes in whole blood as determined by the illustrated embodiment. Vertical dashed lines indicate the bins $B_0$ to $B_7$. For each particle, the pulse height analyser determines the specific pulse height interval or bin of the pulse height generated by the particle for determination of the total number of particles in each interval or bin. Variations in the diameter of the aperture will stretch or compress the particle distribution along the x-axis of the plotted curve making it desirable to adjust the threshold voltages correspondingly for improved accuracy of the determination. Since a priori knowledge is available on the shape of the cell size distribution of whole blood, it is possible to reposition the threshold voltages to fit the known general shape.

In the illustrated embodiment, a measurement cycle starts with a short interval, e.g. ranging from 1 to 100 seconds, such as 10 seconds, of particle size determinations on a first part of the blood sample without calibration of the threshold voltages. Based on the collection of data into 8 bins the threshold voltages are adjusted as already explained. In the illustrated embodiment, the algorithm for the threshold adjustment has been found empirically by analysis of data from more than 100 samples. The data was also collected with a digital signal processor with 1024 sized categories corresponding to a dynamic range of 0 Volts to 3 Volts in order to make a visual identification of the maximum size of granulocytes possible. According to the best data fit, the threshold voltages are adjusted by adjustment of the gain of the electrode pulses according to:

$$\Delta Gain = C_1 \frac{W_4}{W_3 + W_4 + W_5 + W_6} + C_2$$

wherein $W_i$ is the particle count in bin i, and $C_1$ and $C_2$ are constants. This algorithm has the characteristic that ΔGain ranges from $C_2$ to $(C_1+C_2)$.

Figure 8:
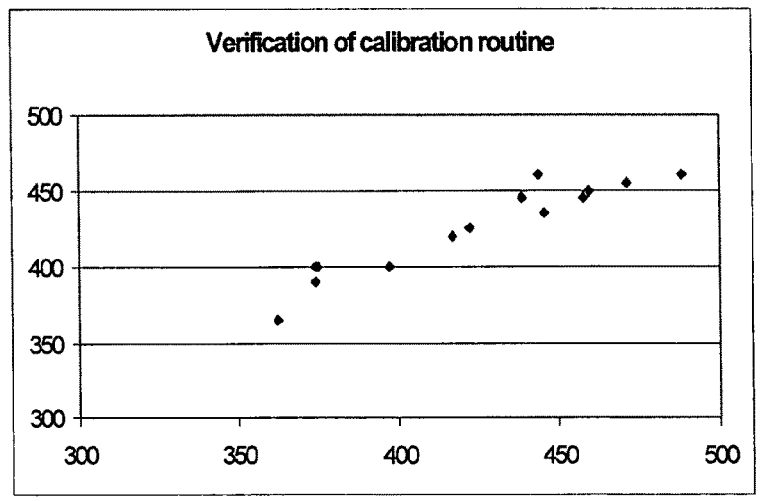
FIG. 8 is a plot of the correlation between visual adjustment and algorithm adjustment of the size distribution.

FIG. 8 shows a plot illustrating verification of the calibration routine as described above. The vertical axis shows the upper limit of bin $B_5$ as determined by visual inspection of the high resolution size distribution, c.f. FIG. 2, and the horizontal axis shows the upper limit of bin $B_5$ as determined by the calibration routine. The correlation between the visual calibration and the ΔGain algorithm above was 0.95. The constants $C_1$ and $C_2$ may be determined empirically by optimizing the values of $C_1$ and $C_2$ in the formulae to the best possible fit of the upper limit of bin $B_5$ as determined by the formulae to the corresponding visually observed value.

Figure 9:
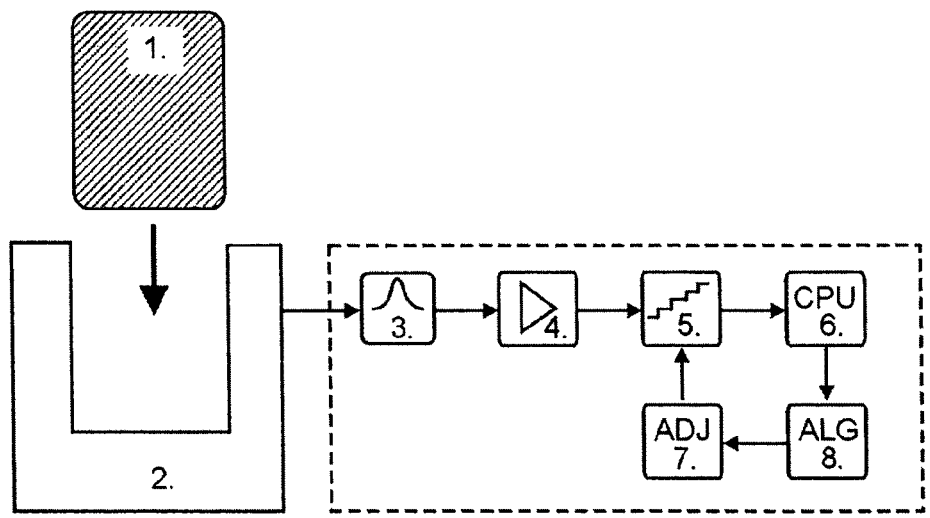
FIG. 9 is a blocked schematic of the haematology analyser of FIG. 1.

FIG. 9 is a blocked schematic of the haematology analyser shown in FIG. 1. The cartridge 1 is inserted into the docking station 2 with the electronic interface. The signals from the cartridge 3 are received and amplified 4 and the particle size is compared to a set of preset threshold levels 5. The result is the bin of the particle, which is collected and stored in the controller 6. After a short count session, the collected data is entered into the algorithm 8, and the calculated result is used for setting an adjustment circuitry 7 that controls the thresholds.

Figure 10:
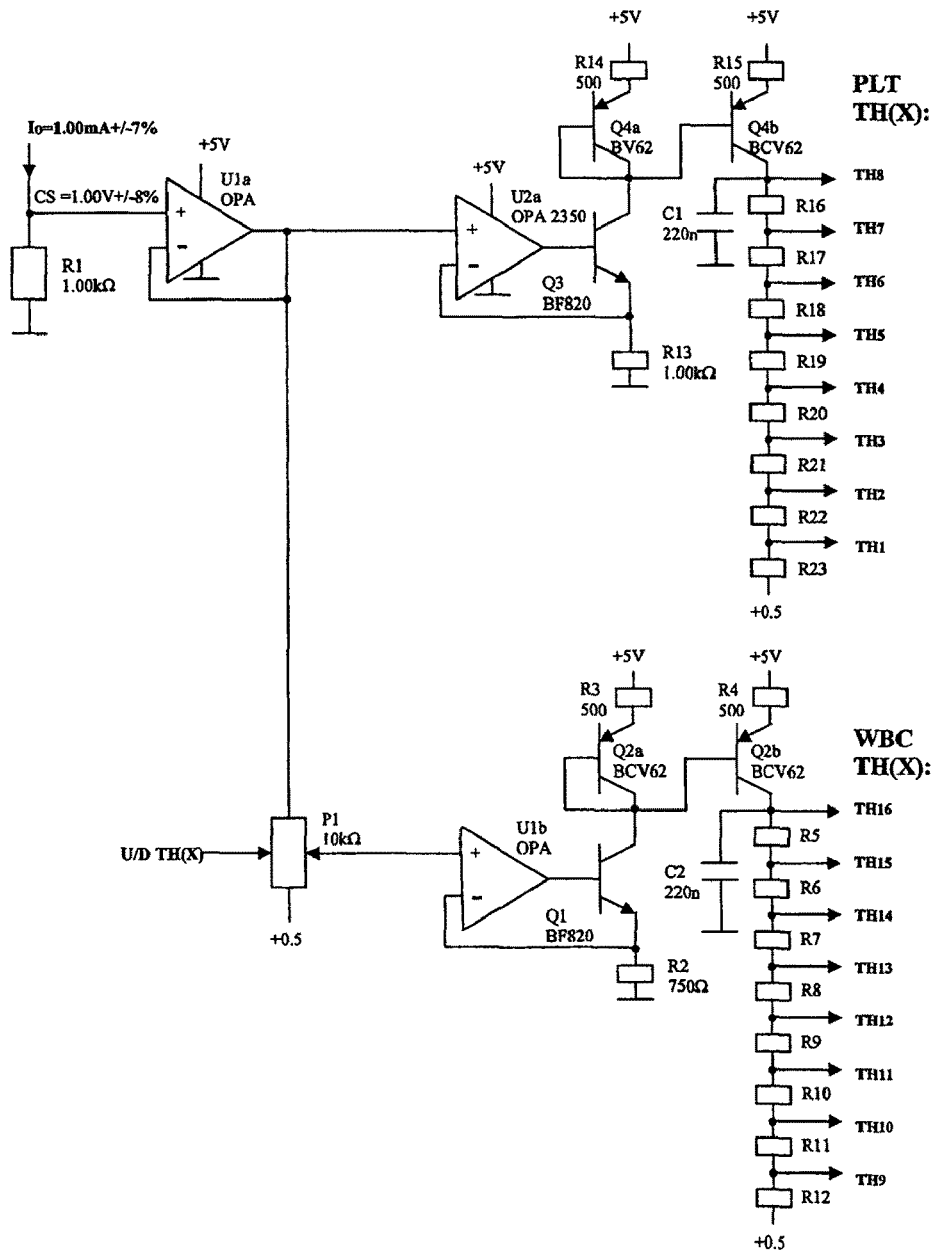
FIG. 10 is a diagram of the electronic circuit for generation of threshold voltages of the haematology analyser of FIG. 1.

FIG. 10 illustrates a circuit 7 of a preferred embodiment for generation of threshold voltages. $I_o$ is the generated constant electrode current of 1.00 mA±7%. $I_o$ generates a voltage $V_o$ across $R_1$. $U_{1a}$ is a voltage follower, and $U_{2a}$ generates the same voltage $V_o$ across $R_{13}$ so that $I_{TH1}$ is substantially equal to $I_o$. It should be noted that the threshold voltages $P_1$ to $P_8$ generated in the voltage divider $R_{18}$ to $R_{23}$ by $I_{TH1}$ vary proportionally to $I_o$ but apart from this variation, the threshold voltages $TH_1$ to $TH_8$ are fixed. These threshold voltages are used for counting platelets.

Further, the output voltage of the voltage follower is voltage divided by the programmable potentiometer $P_1$, and $U_{1b}$ generates the divided voltage $U_{P1}$ across $R_2$. The current generated through $R_2$ is mirrored into the voltage divider $R_5$ to $R_{12}$ generating the threshold voltages $TH_9$ to $TH_{16}$. These threshold voltages are used for categorization of white blood cells. It should be noted that these threshold voltages vary proportionally to $I_o$ so that influence of $I_o$ variations on determined pulse heights is substantially eliminated. Further, the threshold voltages are also adjustable via the control line U/D TH(X) for digital up/down adjustment of the potentiometer $P_1$. The adjustment is performed during calibration as described above.

The invention claimed is:

1. An impedance particle counter for determining a particle size distribution in a sample containing the particles by determination of the corresponding pulse height distribution, the impedance particle counter having a controller that is programmed for
   a) controlling the impedance particle counter to count particles contained in a first part of the sample to determine the number of particles in each bin of a predetermined set of bins having different bin limits,
   b) adjusting bin upper and lower limits in accordance with the determined number of particles in each bin and based on a priori knowledge of a typical particle size distribution of the type of sample in question, and
   c) counting particles contained in a second part of the sample based on the adjusted bin upper and lower limits to determine the number of particles in each bin,
   wherein at least one of the bin limits are adjusted according to the formula:

$$UpperLimit(B_i) = C_1 \frac{a_0 \cdot W_0 + a_1 \cdot W_1 + \ldots + a_i \cdot W_i}{b_0 \cdot W_0 + b_1 \cdot W_1 + \ldots + b_i \cdot W_i} + C_2$$

wherein C1 and C2 are constants, Bi is the i'th predetermined bin and Wi is the number of particle counts in the i'th bin, and UpperLimit(Bi) is the adjusted upper limit of the i'th bin.

2. An impedance particle counter for determining a particle size distribution in a sample containing the particles by determination of the corresponding pulse height distribution, the impedance particle counter having a controller that is programmed for
   a) controlling the impedance particle counter to count particles contained in a first part of the sample to determine the number of particles in each bin of a predetermined set of bins having different bin limits,
   b) adjusting bin upper and lower limits in accordance with the determined number of particles in each bin and based on a priori knowledge of a typical particle size distribution of the type of sample in question, and
   c) counting particles contained in a second part of the sample based on the adjusted bin upper and lower limits to determine the number of particles in each bin,
   wherein at least one of the bin endpoints are adjusted according to the formula:

$$UpperLimit(B_i) = C_1 \frac{W_{i-1}}{W_{i-2} + W_{i-1} + W_i + W_{i+1}} + C_2$$

wherein C1 and C2 are constants, Bi is the i'th predetermined bin and Wi is the number of particle counts in the i'th bin, and UpperLimit(Bi) is the adjusted upper limit of the i'th bin.

* * * * *